(12) United States Patent
Zhao (10) Patent No.: US 7,385,052 B2
(45) Date of Patent: Jun. 10, 2008

(54) PROCESS FOR THE PRODUCTION OF MULTIPLE CROSS-LINKED HYALURONIC ACID DERIVATIVES

(75) Inventor: Xiaobin Zhao, Edinburgh (GB)

(73) Assignee: Mentor Biopolymers Ltd., Edinburgh (GB)

( * ) Notice: Subject to any disclaimer, the term of this patent is extended or adjusted under 35 U.S.C. 154(b) by 475 days.

(21) Appl. No.: 09/920,286

(22) Filed: Aug. 2, 2001

(65) Prior Publication Data

US 2002/0091251 A1 Jul. 11, 2002

Related U.S. Application Data

(63) Continuation of application No. PCT/GB00/00321, filed on Feb. 3, 2000.

(30) Foreign Application Priority Data

Feb. 3, 1999 (GB) .................................. 9902412

(51) Int. Cl.
*C07H 5/04* (2006.01)
*C07H 5/06* (2006.01)
*C08B 37/00* (2006.01)
*A01N 43/04* (2006.01)
*A61K 31/715* (2006.01)

(52) U.S. Cl. ................. 536/55.3; 536/55; 536/55.1; 536/123.1; 536/124

(58) Field of Classification Search ............... 536/18.7, 536/55, 55.1, 55.2, 55.3, 123.1, 124; 514/54
See application file for complete search history.

(56) References Cited

U.S. PATENT DOCUMENTS

| 4,582,865 A | * | 4/1986 | Balazs et al. ................... 524/29 |
| 4,957,744 A | * | 9/1990 | della Valle et al. .......... 424/401 |
| 4,963,666 A | | 10/1990 | Malson |
| 5,411,874 A | | 5/1995 | Ellwood et al. ............... 435/84 |
| 5,510,121 A | | 4/1996 | Rhee et al. ................... 424/520 |
| 5,550,187 A | | 8/1996 | Rhee et al. ................. 525/54.1 |
| 5,578,661 A | | 11/1996 | Fox et al. ....................... 524/27 |
| 5,644,049 A | | 7/1997 | Giusti et al. .................. 536/53 |
| 5,690,961 A | * | 11/1997 | Nguyen ....................... 424/488 |
| 5,800,541 A | | 9/1998 | Rhee et al. .................... 623/11 |
| 6,096,727 A | | 8/2000 | Kuo et al. |
| 2002/0049281 A1 | * | 4/2002 | Zhao et al. ................. 525/54.3 |

FOREIGN PATENT DOCUMENTS

| EP | 0 161 887 A2 | 11/1985 |
| EP | 0 341 745 A1 | 11/1989 |
| WO | WO97/04012 | 2/1997 |
| WO | WO98/02204 | 1/1998 |
| WO | WO 00/54762 | 9/2000 |

OTHER PUBLICATIONS

Hardingham, T.E. and Muir, H., "The specific interaction of hyaluronic acid with cartilage proteoglycans," *Biochim. Biophys. Acta* 279:401-405, Elsevier Publishing Company (1972).

Tomihata, K. and Ikata, Y., "Crosslinking of hyaluronic acid with water-soluble carbodiimide," *J. Biomed Mater. Res.* 37:243-251, John Wiley and Sons, Inc. (Nov. 1997).

English language abstract of Japanese Publication No. 08157378, JPO (1996).

Tomihata et al., "Preparation of Cross-Linked Hyaluronic Acid Films of Low Water Content," Biomaterials 18, Elsevier Science Limited, (1997), pp. 189-195.

Bulpitt et al., "New strategy for chemical modification of hyaluronic acid: Preparation of functiontalized derivatives and their use in the formation of novel biocompatible hydrogels," *J. Biomed. Mater. Res.* 47:152-169, 1999.

* cited by examiner

*Primary Examiner*—Patrick Lewis
(74) *Attorney, Agent, or Firm*—Fish & Richardson P.C., P.A.

(57) ABSTRACT

The present invention relates to a process for the production of cross-linked hyaluronic acid (HA) derivatives, in particular multiple, e.g. double cross-linked hyaluronic acid derivatives. The invention also provides novel cross-linked HA derivatives, products containing them and their uses in medical and pharmaceutical and cosmetic applications.

16 Claims, 4 Drawing Sheets

PROCESS FOR THE PRODUCTION OF MULTIPLE CROSS-LINKED HYALURONIC ACID DERIVATIVES

This application is a continuation of International application No. PCT/GB00/00321, filed on 3 Feb. 2000, which was published under PCT Article 21(2) in English and which is fully incorporated herein by reference.

The present invention relates to a process for the production of hyaluronic acid (HA) derivatives, in particular multiple, eg double cross-linked hyaluronic acid derivatives, to novel cross-linked derivatives so obtained, to products containing them and their uses in cosmetic, medical and pharmaceutical applications.

HA is a member of a class of polymers known as glycosaminoglycans. HA is a long chain linear polysaccharide and is usually present as the sodium salt which has a molecular formula of $(C_{14}H_{20}NNaO_{11})_n$ where n can vary according to the source, isolation procedure and method of determination. However, molecular weights of up to $14 \times 10^6$ have been reported.

HA and its salts can be isolated from many sources including human umbilical cord, rooster combs and nearly all connective matrices of vertebrate organisms. HA is also a capsular component of bacteria such as *Streptococci*; it may therefore also be obtained by fermentation methods. For example, the present applicant's U.S. Pat. No. 5,411,874 describes a method for producing hyaluronic acid by continuous fermentation of *Streptococcus egui*.

HA is non-immunogenic and therefore has great potential in medicine. Because of its visco-elastic properties HA having a high molecular weight (over 1 million) has been found to be particularly useful in a variety of clinical fields, including wound treatment, ophthalmic surgery and orthopaedic surgery. HA is also potentially useful in a variety of non-medical fields, such as cosmetic applications.

However, the use of HA in certain of these applications is limited by the fact that following administration to humans HA is readily degraded by enzymes such as hyaluronidases and by free radicals. Furthermore, HA is soluble in water at room temperature, which can also make it less suited to certain applications. Various attempts have therefore been made to prepare more stable forms of HA, in particular by cross-linking the HA molecules.

Thus, U.S. Pat. No. 4,582,865 (Biomatrix Inc.) describes the preparation of cross-linked gels of hyaluronic acid which are formed by cross-linking HA either by itself or mixed with other hydrophilic polymers using divinyl sulfone as the cross-linking agent. It appears that in this case the cross-linking occurs via the hydroxyl groups of HA.

U.S. Pat. No. 5,550,187 (Collagen Corporation) describes a method for preparing cross-linked biomaterial compositions which involves mixing a biocompatible polymer, which is preferably collagen but may be selected from other polymers including hyaluronic acid, with a sterile dry cross-linking agent such as a synthetic hydrophilic polymer.

U.S. Pat. No. 5,578,661 (Nepera Inc.) describes a gel forming system for use as a wound dressing which is formed from three main components, the first being a water soluble polymer, the second being an acid-containing polymer and the third being a polysaccharide or amino-containing polymer such as hyaluronic acid. In this case the cross-linking appears to be via ion-bonding.

U.S. Pat. No. 5,644,049 (Italian Ministry for Universities and Scientific and Technology Research) describes a biomaterial comprising an inter-penetrating polymer network (IPN) wherein one of the polymer components is an acidic polysaccharide such as hyaluronic acid and the second polymer component may be a synthetic chemical polymer. The two components may be (but are not necessarily) cross-linked.

Tomihata and Ikada have reported cross-linking of HA using a water soluble carbodiimide as cross-linking agent. It was postulated that cross-linking took place via ester groups. The cross-linking reaction was also carried out in the presence of L-lysine methyl ester, which appeared to give additional cross-linking via amide bonds to the lysine ester. (J. Biomed. Mater. Res., 37, 243–251,1997).

U.S. Pat. No. 5,800,541 describes collagen-synthetic polymer matrices prepared using a multiple step reaction. The first step involves reacting collagen with a synthetic hydrophilic polymer; the resulting matrix may then be modified in a second reaction step which may involve cross-linking or conjugating the matrix with a synthetic polymer, coupling biologically active molecules or glycosaminoglycans to the matrix, cross-linking the matrix using conventional chemical cross-linking agents or modifying the collagen in the matrix by means of chemical reaction. In this process, the initial collagen-synthetic polymer matrix appears to be cross-linked via only one type of bond, and the additional process steps serve to introduce further chemical substances which may form different types of bonds. However, it does not appear that any two of the substances forming the product will be linked to each other by more than one type of bond.

International patent application WO 97/04012 (Agerup) describes polysaccharide (which may be inter alia hyaluronic acid) gel compositions which are prepared by forming an aqueous solution of the poylsaccharide, initiating cross-linking in the presence of a polyfunctional cross-linking agent, sterically hindering the cross-linking reaction from being terminated before gelation occurs (eg by diluting the solution) and then reintroducing sterically unhindered conditions (eg by evaporating the solution) so as to continue the cross-linking to a viscoelastic gel. There is no suggestion in this application that different types of bonds are formed in the two cross-linking stages.

None of the aforementioned documents describe products in which molecules of HA are linked to each other by means of two different types of cross-linking bonds.

We have now found that hyaluronic acid may be cross-linked by two different types of cross-linking bonds, to effect a 'double cross-linking'. The formation of different types of bonds is achieved by effecting the cross-linking via different functional groups. The bonds so formed can therefore be described as functional bonds. Thus for example one type of bond may be formed by cross-linking via hydroxyl groups and a different functional bond formed by cross-linking via e.g. carboxyl groups. Such multiple cross-linking has been found to result in a high degree of cross-linking with improved biostability of HA.

In a first aspect therefore, the present invention provides a process for the preparation of multiple cross-linked derivatives of hyaluronic acid, which process comprises cross-linking HA via two or more different functional groups.

The crosslinking of each type of functional group may be effected by contacting HA with one or more cross-linking agents, simultaneously or sequentially, as described in more detail hereinbelow.

In this specification, 'multiple crosslinked HA' refers to a hyaluronic acid derivative wherein a molecule of HA is cross-linked to another molecule of HA by means of two or more different types of functional bond. Similarly, 'double crosslinked HA' refers to a hyaluronic acid derivative wherein a molecule of HA is cross-linked to another molecule of HA by means of two different types of functional bond and 'single crosslinked HA' refers to a hyaluronic acid derivative wherein a molecule of HA is cross-linked to another molecule of HA by means of only one type of functional bond The functional groups which are mainly responsible for cross-linking of HA molecules are the hydroxyl and carboxyl groups. Hydroxyl groups may be cross-linked via an ether linkage and carboxyl groups via an ester linkage. If desired the HA may be chemically modified prior to cross-linking to form other chemically reactive groups. Thus for example HA may be treated with acid or base such that it will undergo at least partial deacetylation, resulting in the presence of free amino groups. Said amino groups may be cross-linked via an amide (—C(O)—NH—); imino (—N=CH—) or amine (—NH—CH—) bond. An imino bond is a precursor of an amine bond and an imino linkage can be converted into an amine linkage in the presence of a reducing agent.

Cross-linking agents which may be used in the process of the present invention include those well-known in the art, for example formaldehyde, glutaraldehyde, divinyl sulfone, a polyanhydride, a polyaldehyde, a polyhydric alcohol, carbodiimide, epichlorohydrin, ethylene glycol diglycidylether, butanediol diglycidylether, polyglycerol polyglycidylether, polyethylene glycol, polypropylene glycol diglycidylether, or a bis-or poly-epoxy cross-linker such as 1,2,3,4-diepoxybutane or 1,2,7,8-diepoxyoctane.

To form an ether linkage the cross-linking agent is preferably selected from formaldehyde, gluteraldehyde, divinyl sulfone and, in alkaline conditions, bis and poly epoxides. Preferably the crosslinker contains a hydrophobic hydrocarbon segment, e.g. 1,2,3,4,-diepoxybutane, or most preferably 1,2,7,8-diepoxyoctane.

To form an ester linkage the cross-linking agent is preferably selected from polyhydric alcohols, carbodi-imides, polyanhydrides, carboxylic acid chlorides and, in acid conditions, bis and poly epoxides. Preferably the crosslinker contains a hydrophobic hydrocarbon segment, e.g. 1,2,3,4,-diepoxybutane, or most preferably 1,2,7,8-diepoxyoctane.

An amide linkage is preferably formed using a cross-linking agent selected from carbodi-imides in the presence of amines, carboxylic acid anhydrides and chlorides (with deacetylated HA), and diisocyanates.

An amine linkage is preferably formed using a cross-linking agent selected from an epoxide, or glutaraldehyde with a reducing agent, in the presence of amino groups in deacylated HA.

An imino linkage (schiff base bond) may be formed using glutaraldehyde in the presence of amino groups in deacylated HA.

A sulfone linkage is preferably formed using a sulfonyl chloride.

In one embodiment of the present invention, the different functional bonds may be formed sequentially, in a multi-step process, which may be achieved either by using a different cross-linking agent for each stage or by using the same cross-linking agent at each stage and adjusting the reaction conditions to control the specific cross-linking reaction required.

Thus, to achieve multiple, e.g. double, cross-linking in a step-wise manner according to the present invention a first cross-linking reaction is carried out, for example using one of the methods described below. When this is complete, or has progressed as far as required, a further cross-linking agent is added to the reaction mixture to effect the second cross-link. The further cross-linking agent may be the same or different from the first. When a different cross-linking agent is employed it will generally be selected such that without changing the reaction conditions, it will form a different type of functional bond. However, when the same cross-linking agent is employed to form both cross-links, the reaction conditions should be adjusted accordingly in order to form a different type of bond. Those skilled in the art will readily be able to select an appropriate cross-linking agent and the appropriate reaction conditions to form the desired bond.

For the avoidance of doubt, it is noted that if the same cross-linking agent is used under the same reaction conditions at each step, this will result in only one type of linkage, i.e. it will give a single cross-linked product, albeit produced in two or more stages.

It will be appreciated that when the two or more functional bonds according to the invention are formed sequentially, i.e. in a multi-stage reaction, the cross-link formed in the first stage of the reaction should be sufficiently strong to withstand the reaction conditions needed to form the second or subsequent cross-link(s). Thus, the stronger of the two (or more) bonds should be formed first. This will be readily apparent to the skilled worker and if necessary can be determined by means of routine experimentation.

Thus, when the cross-links are to be formed via hydroxyl and carboxyl groups it will be recognised that the first-stage cross-linking should be effected via the hydroxyl groups to give an ether linkage and the second-stage cross-linking will then be effected via the carboxyl groups, to give an ester link.

An ether bond may be formed using an epoxide crosslinker under alkaline conditions, preferably at a pH of 10 or more or, providing the HA contains no free amino groups, using glutaraldehyde as the crosslinking agent under acid conditions e.g. pH4 or less. An ester bond may be formed with an epoxide crosslinker under acid conditions e.g. pH4 or less.

Thus, for example, a first cross-linking reaction to form an ether linkage may be carried out using an epoxide such as 1,2 7,8-diepoxyoctane under alkaline conditions, preferably at a pH of 10 or more, for example in the range of pH 10 to pH12. A second cross-linking reaction to form an ester linkage may subsequently be effected employing the same cross-linking agent, and adjusting the pH of the reaction medium to pH4 or less, for example in the range pH 4 to pH2. Alternatively different cross-linking agents may be used in each step, in which case it may not be necessary to adjust the reaction conditions. Thus for example a first cross-linking reaction may be carried out using glutaraldehyde under acidic conditions to form an ether link, followed by reaction with an epoxide cross-linker also under acid conditions to form an ester link.

The ratio of cross-linking agent to HA employed at each stage of this process will generally be in the range 1:10 to 10:1 by weight.

The individual cross-linking reactions may be carried out according to methods known generally in the art.

Thus, the HA utilised as the starting material may be in the form of a film or in solution.

When HA film is employed, this may be suspended in a suitable solvent together with a cross-linking agent. The reaction medium preferably comprises an organic solvent such as acetone, chloroform, or an alcohol e.g. ethanol or isopropanol, admixed with an aqueous acidic or alkaline solution. An acidic solution preferably has a pH of 4 or less and an alkaline solution preferably has a pH of 10 or above. The cross-linking reaction suitably takes place at a temperature in the range of 15 to 30° C. e.g. ambient temperature.

Preferably, when HA film is employed as starting material an ether cross-link is first formed with either an epoxide under alkaline conditions or, providing there are no free amino groups present, glutaraldehyde under acid conditions, followed by formation of an ester cross-link using epoxide under acid conditions. If the HA has been deacetylated to provide free amino groups, a schiff base with an imino linkage can be formed by reacting with glutaraldehyde under acidic conditions. An imino bond can be converted to an amine bond using a reducing agent.

HA may also be employed as an aqueous acidic or alkaline solution to which the cross-linker is added. Under acidic conditions the pH of the starting solution is preferably pH4 or lower and for an alkaline solution the pH is preferably pH10 or above. The concentration of HA is suitably in the range 1 to 10% w/w. The reaction may be effected at a temperature in the range of 15 to 50° C. The time for completion of the cross-linking reaction may in general vary from about an hour to a few days.

Preferably, when an HA solution is employed an ether cross-link is first formed with an epoxide under alkaline conditions, followed by formation of an ester cross-link using an epoxide (preferably the same epoxide as in the first step) under acidic conditions.

Alternatively, HA solution may be subjected to a first cross-linking reaction, the intermediate product dried to form a film and said film subjected to a further cross-linking reaction as described above to give a double cross-linked product in the form of a film. Preferably, to obtain a double cross-linked HA according to this procedure, an ether cross-link is first formed with an epoxide under alkaline conditions, followed by formation of an ester cross-link using an epoxide (preferably the same epoxide as in the first step) under acidic conditions.

In another embodiment of this invention, multiple cross-linking of HA, in particular double cross-linking, may be effected in a single step reaction, by contacting HA simultaneously with two different cross-linking agents, suitable for cross-linking two different functional groups under the same conditions. Thus, for example, to form both ether and ester groups in a single step HA may be contacted with a mixture of glutaraldehyde and 1,2,7,8-diepoxyoctane.

The ratio of cross-linking agent to HA employed at each stage of this process will generally be in the range 1:10 to 10:1 by weight.

The precise nature of the product may be varied by appropriate selection of reaction conditions so as to control the degree of cross-inking and hence the properties of the product. Factors which influence the degree of crosslinking and hence the nature of the final product include the form of the HA starting material employed, the feeding ratio of crosslinking agent to HA, the reaction time, temperature and the pH. The product may be obtained in the form of a gel or film and may be clear or opaque. The water absorption capacity and biostability will vary depending on the precise nature of the product.

A product according to the invention may be obtained in the form of a film or sheet by employing HA starting material in the form of a solution, film or sheet and carrying out the process without stirring. It will be appreciated that when HA is employed in the form of a film or sheet, this will absorb water when placed in aqueous solution such as PBS buffer and swell to form a gel. If desired an intermediate film may optionally be formed after the first cross-linking step, as described above. The product may be clear or opaque, depending upon the degree of cross-linking which occurs. Highly cross-linked HA products are generally opaque and may even be white in colour.

A product according to the invention in the form of a gel may be obtained by hydration of a film, which may for example be prepared as described above. If necessary the film may be subdivided into small pieces to facilitate absorbtion of water.

To obtain a product according to the invention in the form of an opaque gel, the HA starting material may be employed in the form of a solution, film or sheet and the entire process effected with stirring and without forming a film at any stage.

Whichever cross-linking method is used, the completion of the reaction can be routinely controlled by methods well known in the art, for example, the reaction may be terminated by neutralising the reaction mixture and solvent precipitation to obtain a product with the desired degree of cross-linking.

The final product may be isolated from the reaction medium by conventional procedures.

In a preferred embodiment the present invention provides a process for preparing double cross-linked HA, said process comprising contacting HA with one or more cross-linking agents under conditions suitable for forming two different bonds between the HA molecules. Preferably the cross-linking reactions are effected sequentially. Thus, the two-stage process according to the invention comprises:

(a) cross-linking HA via a first functional group and subsequently (b) further cross-linking the product of (a) via a second fictional group, wherein said first and second functional groups represent different chemical entities.

It will be understood that when a product containing more than two different cross-links is required, this may be prepared by an appropriate combination of sequential or simultaneous cross-linking reactions as described above.

Cross-linked HA prepared according to the present invention contains at least two different types of cross-linking bonds, for example both ether and ester bonds.

It is believed that multiple (e.g. double) cross-linked HA derivatives prepared according to the present invention are themselves novel. Thus, in a further aspect the present invention provides mutiple cross-linked HA (i.e. HA cross-linked via two or more different functional bonds) obtainable by the process described hereinbefore. Preferably the invention provides double cross-linked HA obtainable by the process described hereinbefore.

In a further aspect the present invention provides HA cross-linked to itself (i.e. to a further molecule of HA) wherein the HA is crosslinked by at least two different types of bond. Preferably the HA is double cross-linked HA.

Double-crosslinked HA according to the present invention may have a degree of cross-linking in the range 10 to 50%, eg 15 to 30, preferably 20 to 25% (where 100% is represented by cross-linking of all OH groups at the C6 position and all COOH groups at the C5 position). The degree of cross-linking may be measured by elemental analysis or solid state NMR analyis.

The ratios of the different functional bonds in the product will vary depending on the types of functional bonds present and the reaction conditions used to form them. For a double cross-linked product containing ether and ester bonds the ratio of these bonds may vary from 50:50 to 95:5, eg 60:40 to 80:20 ether:ester bonds.

In general a product according to the present invention has a greater degree of cross-linking, that is to say, a denser network of cross-links than does single cross-linked HA. A higher degree of cross-linking has been found to reduce the water absorption capacity of the cross-linked HA, resulting in greater stability in aqueous solution. In addition double cross-linked HA has been found to exhibit greater stability against degradation by hyaluronidase, and against degradation due to free radicals, indicating an increased biostability.

An opaque product according to the present invention generally has a higher degree of cross-linking and hence lower water absorption capacity and greater stability, than a clear product. Such products are suitable for long term implantation.

A clear product e.g. a clear film according to the present invention has higher water absorption capacity than an opaque product and such products are particularly suitable for dermal implants, wound healing (absorption of exudate) and resorbable short-term implantation.

The multi-step process described above is preferred when a highly cross-linked product with low water absorption capacity is desired. Simultaneous cross-linking generally results in a water-insoluble product, but with higher water absorption capacity than a product prepared using a multi-stage (e.g. two-step) process under similar conditions.

Furthermore it has been found that using a first crosslinked HA film for the second cross-linking step provides a product (which may be in film form or may be converted into a gel) with lower water absorption capacity than double cross-linked HA prepared from HA solution under similar crosslinking conditions (ie with no intermediate film formation). Indeed it has been found that the water absorption capacity of the resulting products can vary from 400% to 1000% for film and gel starting materials respectively.

Cross-linked HA derivatives according to the present invention may be used in a variety of pharmaceutical, medical (including surgical) and cosmetic applications.

Thus, they may for example be useful in promoting wound healing, e.g., as a dermal wound dressing.

They may also be useful in preventing adhesion e.g. preventing tissue growth between organs following surgery.

Crosslinked HA derivatives according to the present invention may also find application in the ophthalmic field e.g. for vitreous fluid replacement, as corneal shields for delivery of drugs to the eye or as lenticules.

Crosslinked HA derivatives according to the present invention may also be useful in surgery, for example as solid implants for hard tissue augmentation e.g. repair or replacement of cartilage or bone, or for soft tissue augmentation, as breast implants, or as coating for implants intended for long term use in the body, such as breast implants, catheters, cannulas, bone prostheses, cartilage replacements, mini pumps and other drug delivery devices, artificial organs and blood vessels, meshes for tissue reinforcement, etc. They may also be used as joint lubricants in the treatment of arthritis.

A further use for the derivatives of the present invention is in the delivery of therapeutically active agents including in any of the aforementioned applications. Therapeutically active agents may be chemotherapeutic agents or biologically active factors (e.g. cytokines) and include anti-inflammatory agents, antibiotics, analgesics, anaesthetics, wound healing promoters, cystostatic agents, immunostimulants, immunosuppressants and antivirals The therapeutically active factors may be bound to the crosslinked HA derivative by methods well known in the art.

The crosslinked HA derivatives may be used in a variety of forms including membranes, beads, sponges, tubes, sheets and formed implants.

The invention will now be further illustrated by the following non-limiting examples.

The following procedures were used to measure stability of the products.

METHODOLOGY

Water Absorption Capacity Assessment 20 mg (Wd) of each dried cross-linked samples were immersed in PBS formulation buffer solution for 24 hours to obtain a fully swollen gel. The wet gel was filtered off and the residual water at the surface was removed using tissue paper. The wet gel was weighed to get Ws. Thus the water absorption capacity (WAC) (%) can be calculated according to the following formula:

$$WAC(\%) = (Ws - Wd)/Wd \times 100$$

Resistance to Hyaluronidase Digestion 20 mg crosslinked HA was suspended in 6 ml PBS buffer solution (pH=7.2) containing 1000U hyaluronidase and incubated at 37 degree C. for 24 hours.

After that, the film was removed and rinsed using PBS buffer and all the rinsing solution was collected to obtain total 10 ml solution. This solution was boiled for 30 minutes to get hyaluronidase precipitation. The solution then was centrifiged at 4000 rpm/10 minutes. The supernatant solution was made up to 25 ml using PBS solution in a volumetric flask. The HA concentration was measured using Carbazole assay.

The HA weight loss due to hyaluronidase digestion can be calculated using the following formula:

$$HA \text{ weight loss } (\%) = [HA] \times 25/[HA]o \times 100$$

in which, [HA] is the concentration of HA, [HA]o is the original HA content (mg).

Resistance to Free Radicals

Ferton agents are used to create free radicals, which are formed by 25 microliter 0.1 ascorbic acid and 0.25 microliter 0.1M $H_2O_2$ in 5 ml PBS solution. 20 mg dried sample was added to this solution for digestion. The digestion time is 24 hours at 37° C. After this, the film was removed and rinsed using PBS buffer and all the rinsing solution was collected and made up to 25 ml using PBS buffer in a volumetric flask. The HA concentration was measured using Carbazole assay. The HA weight loss can be calculated using the same formula as hyaluronidase digestion.

EXAMPLE 1

Formation of Double Crosslinked HA Film Starting from HA Film 5 ml of HA (1%) was cast for 4 days at room temperature to get HA film. The resulting film was suspended in a mixture of $CHCl_3$ solvent/acidic or alkaline solution/1,2,7,8-diepoxy-octane or glutaraldehyde cross-linker. The cross-linking reaction was effected at room temperature for a fixed time (24 hr). A further amount of cross-linking agent was added, and if necessary the pH adjusted, and the mixture was allowed to stand at room temperature for a further 24 hours, to effect the second cross-linking reaction. The detailed cross-linking conditions are shown in Table 1. After the cross-linking, the samples were washed with IPA and acetone for three times, immersed into IPA/deionised water (60/40) overnight and then washed with acetone and dried in a 37° C. oven to get a constant weight.

TABLE 1

Formation of Cross-linked HA (CHA) from HA Film

| | First crosslinker | | Second crosslinker | | Time (hour) | Temperature (° C.) | pH | Water absorption capacity (%) |
|---|---|---|---|---|---|---|---|---|
| | Name | feeding ratio* | Name | Feeding ratio* | | | | |
| CHA-2 | G | 2.5/1 | E | 0.75/1 | 24 h/24 h | RT | H+ | 414.4 |
| CHA-8 | E | 0.75/1 | E | 0.75/1 | 24 h/24 h | RT | OH−/H+ | 403.0 |
| CHA-3 | G | 2.5/1 | E | 0.75/1 | 24 h/24 h | RT | H+/OH− | 4430.0 |
| CHA-5 | E | 0.75/1 | G | 2.5/1 | 24 h/24 h | RT | H+ | 1017.2 |
| CHA-9 | E | 0.75/1 | G | 2.5/1 | 24 h/24 h | RT | OH+/H+ | 4400.0 |
| | | | | | Reference Examples | | | |
| CHA-1 | G | 2.5/1 | G | 2.5/1 | 24 h/24 h | RT | H+ | 11132.5 |
| CHA-4 | E | 0.75/1 | E | 0.75/1 | 24 h/24 h | RT | H+ | 781.9 |
| CHA-6 | E | 0.75/1 | E | 0.75/1 | 24 h/24 h | RT | H+/OH− | Dissolved |
| CHA-7 | E | 0.75/1 | E | 0.75/1 | 24 h/24 h | RT | OH− | 11989.1 |

*Feeding ratio: the weight ratio of HA to crosslinker
E: = 1,2,7,8-diepoxyoctane; G: = Glutaraldehyde
H+ represents a pH of about 4; OH− represents a pH of about 10
CHA-1, CHA-4, and CHA-7, were each prepared using the same conditions for each crosslinking step, giving only ether bonds (single cross-linking).

EXAMPLE 2

Formation of Double Crosslinked HA Gel from HA Solution 0.1 g of HA was dissolved in 0.25N NaOH solution or 0.25N HCl solution to obtain HA solutions at 10% or 2.5% concentration. Cross-linking agent was added and the mixture subjected to mechanical stirring. The first cross-linking reaction was effected at 40° C. for a period of about 2 hours. A second cross-linking reaction was effected using a further amount of the same cross-linker, with adjustment of the reaction conditions. Detailed reaction conditions are given in Table 2. After cross-linking, the formed gel was washed with IPA, acetone and extracted with IPA/water overnight and then washed with IPA and acetone respectively for three times. The samples were dried in a 37° C. oven to achieve a constant weight. The product was obtained as an opaque gel.

EXAMPLE 3

Formation of Double Cross-Linked HA (CHA) from HA Solution via HA Film 0.1 g of HA was dissolved in 0.25N NaOH solution or 0.25N HCl solution to obtain HA solutions at 10% or 2.5% concentration. Cross-linking agent was added. The reaction was carried out in a Petri dish with little or no mechanical stirring. The first cross-linking reaction was effected at room temperature for a period of about 48 or about 72 hours. The intermediate product was dried to yield a film or sheet (depending upon the thickness). A second cross-linking reaction was effected using the methodology described in Example 1. Detailed reaction conditions are given in Table 3 below. After cross-linking, the product was washed (×3) with IPA and acetone and extracted with IPA/water overnight and then

TABLE 2

Formation of Cross-linked HA (CHA) from HA Solution

| | First crosslinker | | Second crosslinker | | Time (hr) | Temp (° C.) | pH | Water absorption capacity (%) |
|---|---|---|---|---|---|---|---|---|
| | Name | feeding ratio | Name | feeding ratio | | | | |
| CHA-11 | E | 1/1 | E | 1/1 | 2h/2h | 40 | OH−/H+ | 390.0 |
| CHA-10 | E | 1/1 | E | 1/1 | 2h/2h | 40 | OH−/OH− | 620.0 |
| CHA-12 | E | 1/1 | E | 1/1 | 2h/2h | 40 | H+/OH− | 1830.0 |
| CHA-13 | E | 1/1 | E | 1/1 | 2h/2h | 40 | H+/H+ | dissolved |

E: 1,2,7,8-diepoxyoctane
H+ represents a pH of about 4; OH− represents a pH of about 10 washed with acetone. The samples were dried in a 37° C. oven to achieve a constant weight and the product obtained in the form of a film or sheet.

dimension of polystyrene non-collagen coated Petri dish with a cover. After 24 hours at room temperature, the cover was removed and the cross-linked gel was dried off for 48 hours.

TABLE 3

Formation of Cross-linked HA (CHA) from HA solution via HA film

| | First crosslinker | | Second crosslinker | | | | | Water absorption |
|---|---|---|---|---|---|---|---|---|
| | Name | Feeding ratio | Name | Feeding ratio | Time (hour) | Temperature (° C.) | pH | capacity (%) |
| CHA-17 | E | 0.375/1 | E | 0.5/1 | 72/24 | RT | OH−/H+ | 403.2 |
| CHA-19 | E-1 | 0.375/1 | E | 0.5/1 | 72/24 | RT | OH−/H+ | 1030.0 |
| CHA-14 | E | 0.375/1 | / | / | 72 | RT | Neutral | 2419.1 |
| CHA-15 | E | 0.375/1 | / | / | 72 | RT | H+ | 2128.3 |
| CHA-16 | E | 0.375/1 | / | / | 72 | RT | OH− | 1318.6 |
| CHA-18 | E-1 | 0.375/1 | / | / | 72 | RT | OH− | 2600.4 |

E: 1,2,7,8-diepoxyoctane; E-1: epichlorhydrin
H+ represents a pH of about 4
OH− represents a pH of about 10

TABLE 4

Biostability of crosslinked HA against hyaluronidase and free radicals

| | WEIGHT LOSS(%) | |
|---|---|---|
| NO | Hyaluronidase digestion | Ferton digestion (free radical) |
| CHA-16 | 10.45 ± 0.21 | 7.89 ± 1.92 |
| CHA-17 | 1.45 ± 0.92 | 5.63 ± 2.73 |

EXAMPLE 4

0.1 gm HA were dissolved in 2 ml 1N NaOH solution overnight to get 5% HA alkaline solution. To this solution was added 0.2 ml 1,2,7,8-diepoxyoctane. 0.2 ml chloroform was then added whilst stirring at 40° C. for 30 minutes. After forming the ether cross-linkage, 2.2 ml 1N HCl was added to change the pH of the solution to between 3–4. A further 0.2 ml 1,2,7,8-diepoxyoctane was added and 0.2 ml chloroform was then added whilst stirring at 40° C. for 30 minutes. After the ester cross-linkage, the formed gel was precipitated with 20 ml acetone and purified according to the same procedure as detailed in Example 2.

EXAMPLE 5

To 5 ml HA/NaOH (1N) solution, 0.5 ml epichlorhydrin and 0.2 ml chloroform were added and mixed at room temperature for 10 minutes. The solution was cast in a petri dish and allowed to dry as a film of cross-linked HA (CHA-18). After neutralisation with 1N HCl, the CHA-18 sample was suspended in 20 ml chloroform/0.1N acidic aqueous solution (3/1 v/v) and 0.2 ml 1,2,7,8-diepoxyoctane was added and allowed to react at room temperature for 24 hours. The resulting sample, CHA-19, was purified according to the same procedure detailed in Example 1.

EXAMPLE 6

20 ml of 2.5% HA/NaOH (1.0N) solution was mixed with varied volumes of 1,2,7,8-diepoxyoctane for 5 minutes under stirring. The mixed solution was then spread on to a 7 cm The dried film with controllable thickness was neutralised with acetone/HCl solution and purified with acetone/$H_2O$, acetone and IPA. Then the first cross-linked sheet-like material was put into an acetone/HCl solution at pH 5 and 0.4 ml 1,2,7,8-diepoxyoctane for another 24 hours cross-linking at room temperature. The obtained sheet was purified with acetone/water, acetone, and IPA/water, IPA several times.

The obtained double cross-linked HA sheet is insoluble in water and was found to pick up ten-folds of water to form a transparent gel. It also shows very good mechanical strength, which is an important feature for tissue engineering.

Solid State $^{13}C$ NMR Analysis of HA Samples

Figure 1:
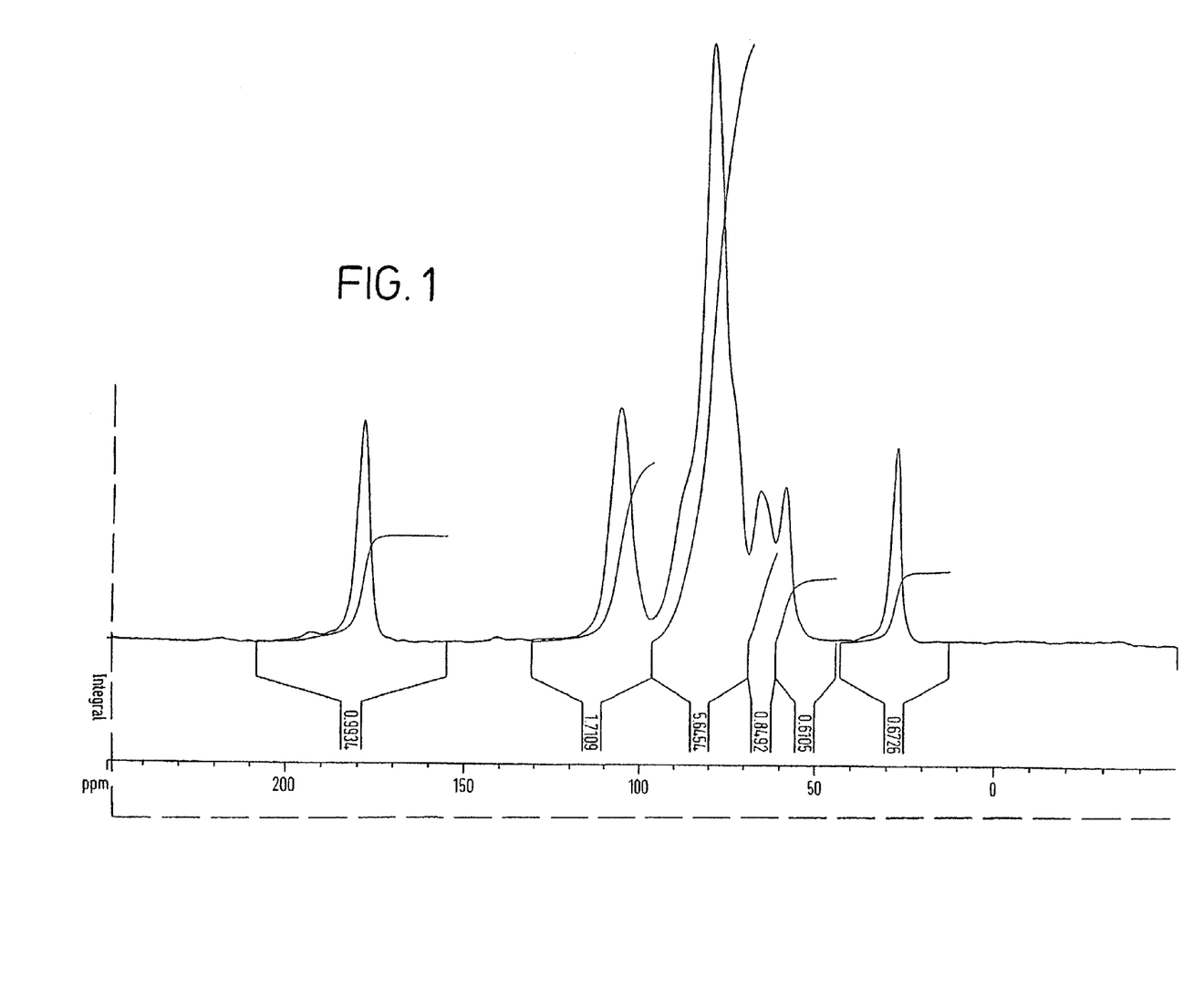
FIG. 1 is a graph showing a solid state $^{13}C$ NMR spectrum of hyaluronic acid.
Figure 2:
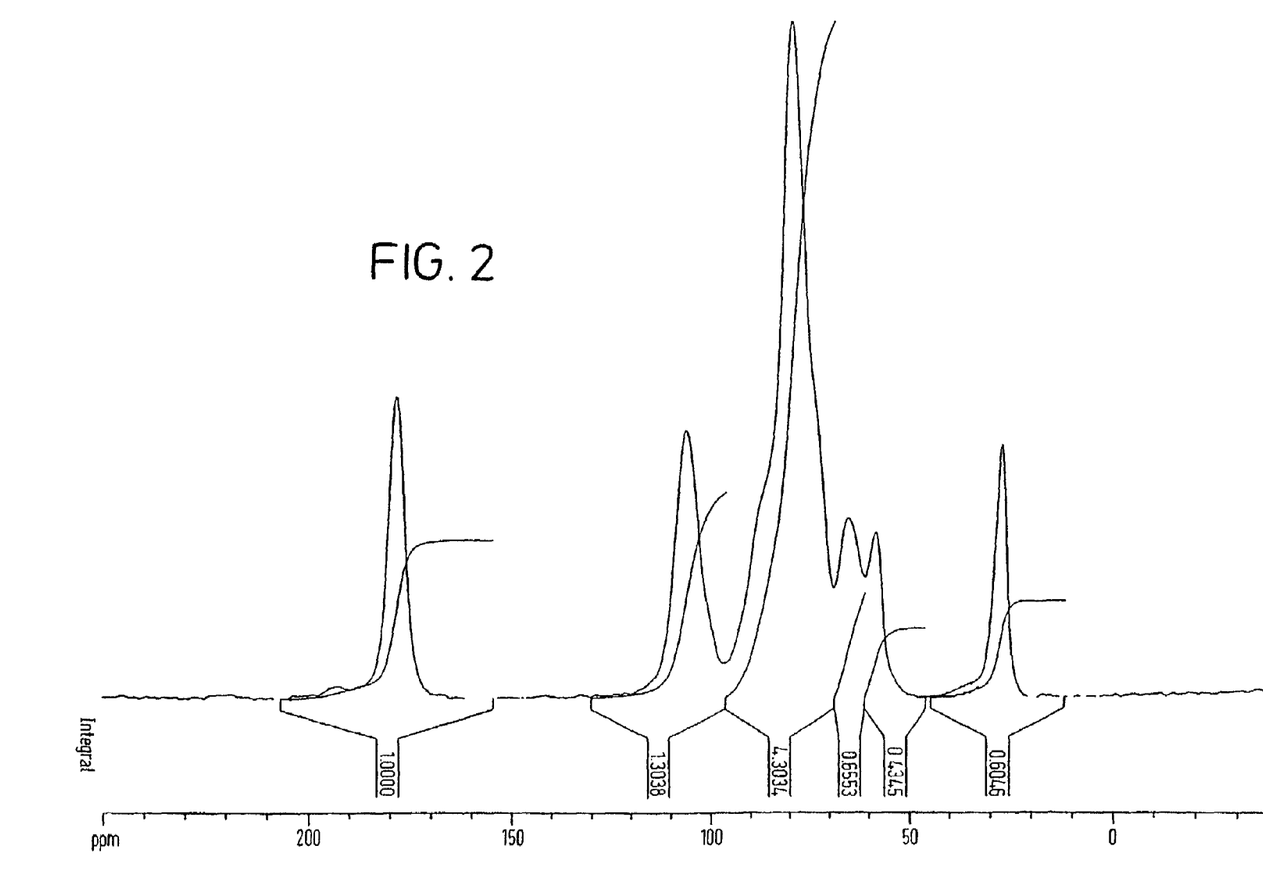
FIG. 2 is a graph showing a solid state $^{13}C$ NMR spectrum of a singly cross linked film of hyaluronic acid that was cut into fine mesh for NMR analysis.
Figure 3:
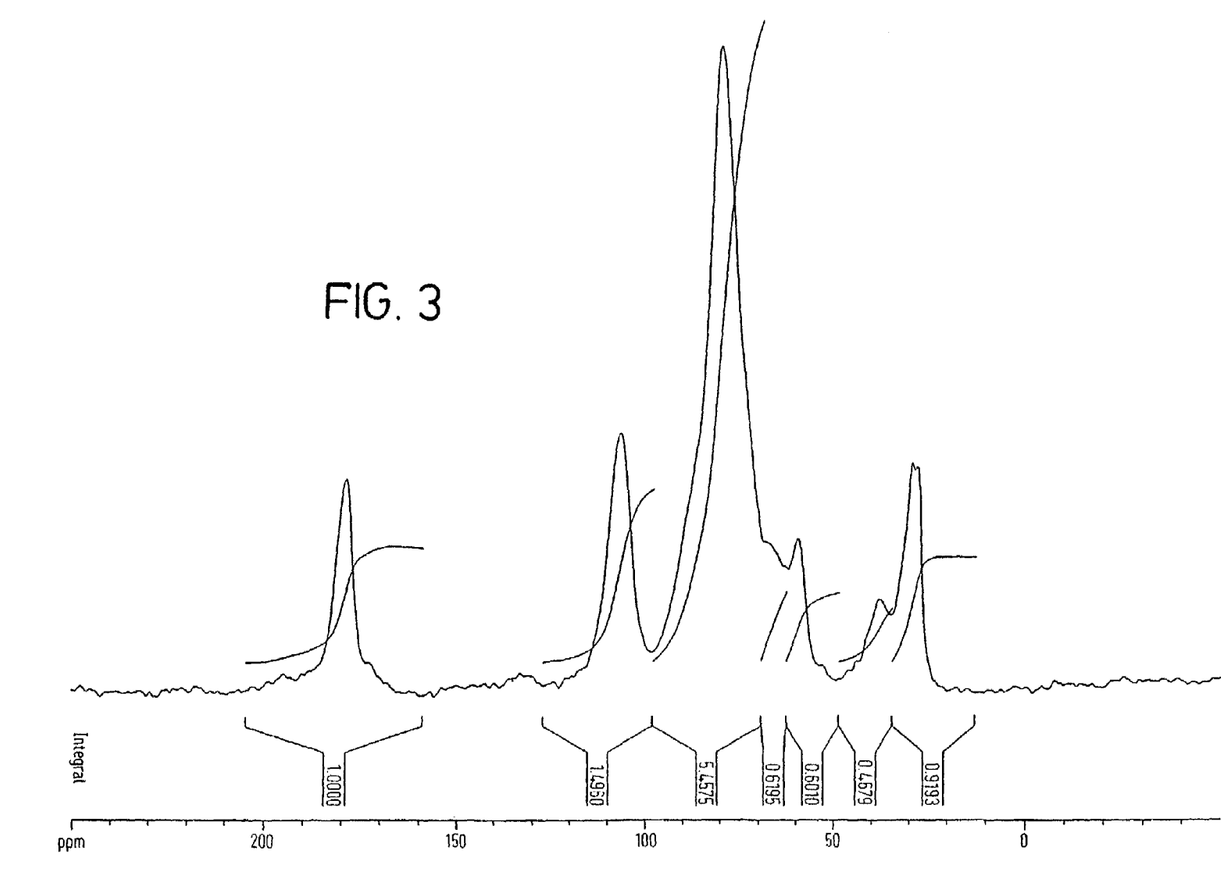
FIG. 3 is a graph showing a solid state $^{13}C$ NMR spectrum of a double cross linked hyaluronic acid gel that was milled to a fine powder for NMR analysis.
Figure 4:
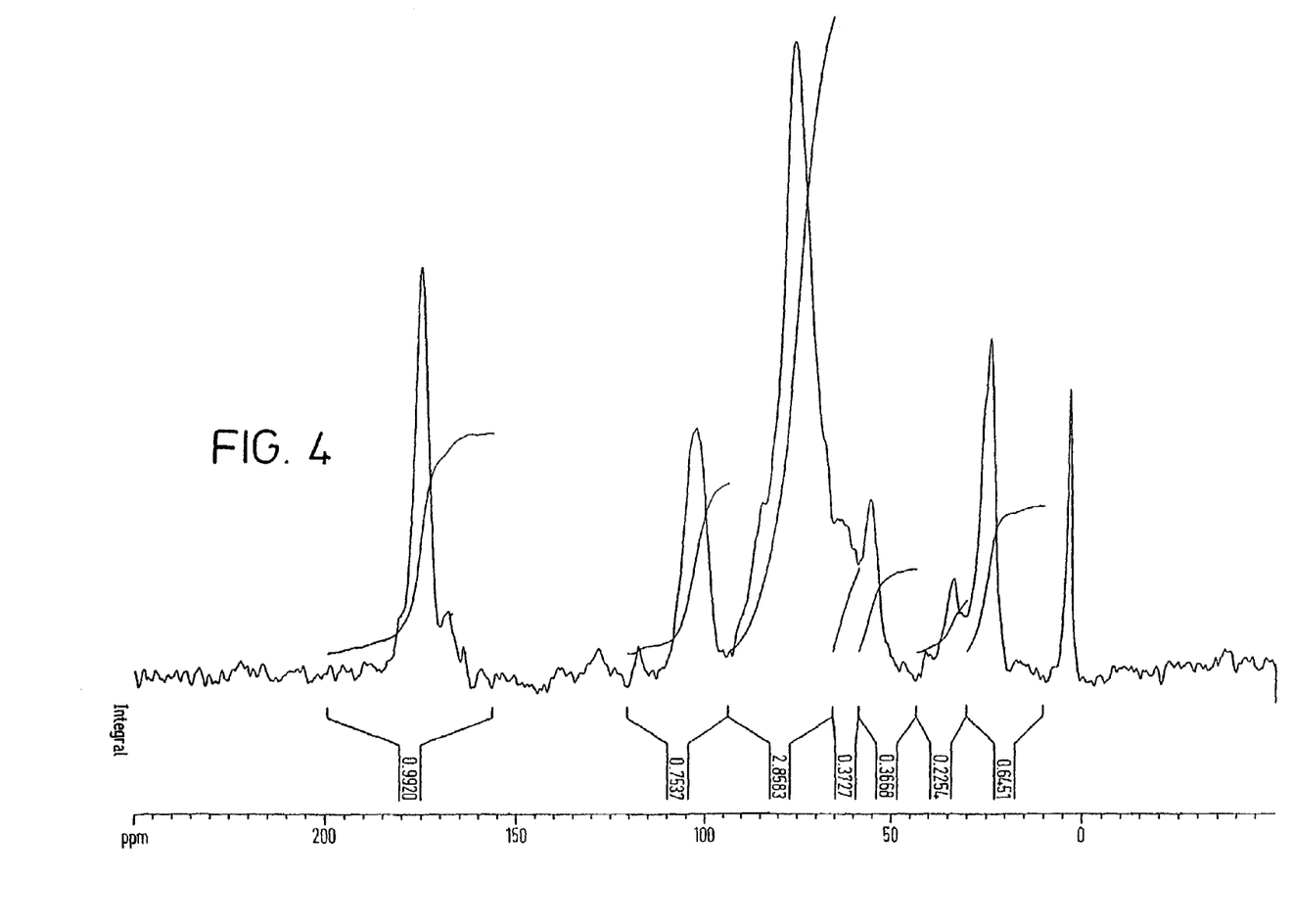
FIG. 4 is a graph showing a solid state $^{13}C$ NMR spectrum of the double cross linked hyaluronic acid powder shown in FIG. 3 in combination with an internal standard, tetrakis (trimethyl)silane, which has a chemical shift of 3.2 ppm.

The solid-state $^{13}C$ NMR analysis of the hyaluroan and the two double cross linked samples was carried at 50 MHz using an Advance 200 spectrometer. The spectra obtained using a contact time of 1 ms in the standard cross polarisation (CP) pulse sequence are shown in FIGS. 1–3. A spectrum of sample No. 3 containing the internal standard, tetrakis(trimethyl)silane (TKS, chemical shift of 3.2 ppm), was also obtained using a contact time of 5 ms (FIG. 4). The peak assignments referenced to TKS are as follows.

| | Chemical shift, ppm |
|---|---|
| C═O in carboxyl and acetyl | 170–180 |
| C═O in ester for modified samples | 165–170 (shoulder) |
| $C_1$ | 95–110 |
| $C_2$–$C_5$ plus OCH and $OCH_2$ in modifier | 65–90 |
| $C_6$ | 60–65 |
| C—N | 53–60 |
| $CH_2$ in modifier not bound to O | 20–40 |
| $CH_3$ in acetyl | 20–25 |

Sample 1 (FIG. 1) is pure hyaluronic acid without modification. The actual formulations for sample 2 and sample 3 are shown in following Table:

|  | FIRST CROSSLINKING | | | | SECOND CROSSLINKING | | | |
| --- | --- | --- | --- | --- | --- | --- | --- | --- |
|  | feeding ratio | pH | Reaction temperature (°C.) | Reaction time (hours) | feeding ratio | pH | Reaction temperature (°C.) | Reaction time (hours) |
| Sample 2 | 3/1 | 10 | RT | 72 | | | | |
| Sample 3 | 1/2 | 10 | RT | 2 hours | 1/2 | 4 | RT | 2 hours |

Sample 2 (FIG. 2): prepared according to the method of Example 3 but without the second crosslinking. The feeding ratio is the amount of HA to 1,2,7,8-diepoxyoctane. The formed film was cut into fine meshes for NMR analysis.

Sample 3 (FIGS. 3 and 4): prepared according to the method of Example 2 to form a gel, which was milled to a fine powder for NMR analysis.

The invention claimed is:

1. A process for the preparation of multiple cross-linked hyaluronic acid (HA), which process comprises covalently cross-linking HA via two or more different functional groups, wherein said cross-linking is effected by contacting HA with one or more chemical cross-linking agents so as to form two or more different types of functional bonds between HA molecules, wherein said two or more different types of functional bonds are selected from the group consisting of ether, ester, sulfone, amine, imino, and amide bonds, and wherein an ether bond is formed using a glutaraldehyde cross-linking agent under acidic conditions.

2. A process for the preparation of multiple cross-linked HA, which process comprises covalently cross-linking HA via two or more different functional groups, wherein said cross-linking is effected by contacting HA with one or more chemical cross-linking agents so as to form two or more different types of functional bonds between HA molecules, wherein said two or more different types of functional bonds are selected from the group consisting of ether, sulfone, amine, imino, and amide bonds.

3. A process according to claim 2, wherein at least one functional bond is an ether bond formed using a cross-linking agent selected from the group consisting of bis epoxides and poly epoxides under alkaline conditions.

4. A process according to claim 2, wherein the cross-linking agent is 1,2,3,4-diepoxybutane or 1,2,7,8-diepoxyoctane.

5. A process for the preparation of multiple cross-linked HA, which process comprises covalently cross-linking HA via two or more different functional groups, wherein cross-linking is effected by contacting HA with one or more chemical cross-linking agents so as to form two or more different types of functional bonds between HA molecules, wherein said two or more different types of functional bonds are selected from the group consisting of ester, sulfone, amine, imino, and amide bonds.

6. A process according to claim 5, wherein at least one functional bond is an ester bond formed using a cross-linking agent selected from the group consisting of bis epoxides and poly epoxides under acidic conditions.

7. A process according to claim 5, wherein the cross-linking agent is 1,2,3,4-diepoxybutane or 1,2,7,8-diepoxyoctane.

8. A process for the preparation of multiple cross-linked HA, which process comprises covalently cross-linking HA via two or more different functional groups, wherein said cross-linking is effected by contacting HA with one or more chemical cross-linking agents so as to form two or more different types of functional bonds between HA molecules, wherein said two or more different types of functional bonds are selected from the group consisting of ether, ester, sulfone, amine, imino, and amide bonds, and wherein said process comprises contacting said HA with a first cross-linking agent in a reaction mixture so as to form a first type of functional bond, and adding to said reaction mixture a further amount of said first cross-linking agent or a second cross-linking agent so as to form a second type of functional bond.

9. A process according to claim 8, wherein said HA is contacted with said first cross-linking agent under alkaline conditions.

10. A process according to claim 9, wherein said first cross-linking agent is a bis epoxide or a poly epoxide.

11. A process according to claim 9, wherein said first cross-linking agent is 1,2,3,4-diepoxybutane or 1,2,7,8-diepoxyoctane.

12. A process according to claim 8, wherein said first cross-linking agent is a bis epoxide or a poly epoxide, and wherein said second cross-linking agent is glutaraldehyde.

13. A process according to claim 8, wherein the cross-linking of each type of functional group is effected sequentially.

14. A process according to claim 8, wherein the cross-linking of each type of functional group is effected simultaneously.

15. A process according to claim 8, comprising adding to said reaction mixture a second cross-linking agent so as to form a second type of functional bond.

16. A process according to claim 9, further comprising adding a further amount of said first cross-linking agent to said reaction medium under acidic conditions.

* * * * *